US009706907B2

(12) United States Patent
Gumbs et al.

(10) Patent No.: US 9,706,907 B2
(45) Date of Patent: Jul. 18, 2017

(54) REMOTE ENDOSCOPE HANDLE MANIPULATION

(71) Applicant: The Trustees of Columbia University in the City of New York, New York, NY (US)

(72) Inventors: Andrew A. Gumbs, Brooklyn, NY (US); Luca Milone, New York, NY (US)

(73) Assignee: Institute for Cancer Research, Philadelphia, PA (US)

( * ) Notice: Subject to any disclaimer, the term of this patent is extended or adjusted under 35 U.S.C. 154(b) by 1113 days.

(21) Appl. No.: 13/852,426

(22) Filed: Mar. 28, 2013

(65) Prior Publication Data
US 2014/0296633 A1    Oct. 2, 2014

Related U.S. Application Data

(63) Continuation-in-part of application No. 12/866,473, filed on Nov. 3, 2010, now Pat. No. 8,409,080.

(51) Int. Cl.
*A61B 1/00* (2006.01)
*A61B 1/005* (2006.01)
*A61B 34/30* (2016.01)

(52) U.S. Cl.
CPC .......... *A61B 1/0052* (2013.01); *A61B 1/0016* (2013.01); *A61B 1/00039* (2013.01); *A61B 1/0057* (2013.01); *A61B 1/00105* (2013.01); *A61B 1/00133* (2013.01); *A61B 1/00006* (2013.01); *A61B 2034/301* (2016.02)

(58) Field of Classification Search
CPC .............. A61B 1/00133; A61B 1/0016; A61B 1/00039; A61B 1/00006; A61B 1/00526; A61B 1/0052; A61B 1/00066

USPC ......................................................... 600/102
See application file for complete search history.

(56) References Cited

U.S. PATENT DOCUMENTS

| | | |
|---|---|---|
| 4,593,679 A | 6/1986 | Collins |
| 4,919,112 A | 4/1990 | Siegmund |
| 4,941,454 A | 7/1990 | Wood et al. |
| 5,347,989 A | 9/1994 | Monroe et al. |
| 5,524,180 A | 6/1996 | Wang et al. |
| 5,540,649 A * | 7/1996 | Bonnell ................ A61B 90/50 294/106 |
| 5,634,466 A | 6/1997 | Gruner |

(Continued)

FOREIGN PATENT DOCUMENTS

| | | |
|---|---|---|
| EP | 1825801 | 8/2007 |
| JP | 7275222 | 10/1995 |

OTHER PUBLICATIONS

European Search Report dated Jul. 30, 2012 from counterpart application, EP 09 70 7539.

*Primary Examiner* — John P Leubecker
(74) *Attorney, Agent, or Firm* — Stradley Ronon Stevens & Young, LLP

(57) ABSTRACT

Systems and methods permit remote control of the operation of an endoscope. The system includes a control housing that removably attaches to an endoscope, with the housing including actuators and manipulators that engage with a control device of the endoscope in order to operate the control device. The system includes an axial roller that may be used to control the depth of the endoscope shaft within a patient's body.

21 Claims, 9 Drawing Sheets

(56) References Cited

U.S. PATENT DOCUMENTS

| | | | |
|---|---|---|---|
| 5,779,623 A * | 7/1998 | Bonnell | A61B 90/50 414/431 |
| 5,951,461 A | 9/1999 | Nyo et al. | |
| 6,004,263 A | 12/1999 | Nakaichi et al. | |
| 6,059,719 A | 5/2000 | Yamamoto et al. | |
| 6,358,199 B1 * | 3/2002 | Pauker | A61M 25/0113 600/102 |
| 6,371,907 B1 | 4/2002 | Hasegawa et al. | |
| 6,468,265 B1 | 10/2002 | Evans et al. | |
| 6,569,084 B1 | 5/2003 | Mizuno et al. | |
| 6,726,675 B1 * | 4/2004 | Beyar | A61M 25/0105 600/106 |
| 6,858,005 B2 | 2/2005 | Ohline et al. | |
| 7,008,376 B2 | 3/2006 | Ikeda et al. | |
| 7,435,216 B2 | 10/2008 | Kwon et al. | |
| 7,578,786 B2 | 8/2009 | Boulais et al. | |
| 7,780,593 B2 | 8/2010 | Ueno et al. | |
| 7,828,723 B2 | 11/2010 | Ueno et al. | |
| 7,850,642 B2 | 12/2010 | Moll et al. | |
| 7,918,861 B2 | 4/2011 | Brock et al. | |
| 8,118,732 B2 | 2/2012 | Banik et al. | |
| 8,409,080 B2 * | 4/2013 | Gumbs | A61B 1/0016 600/118 |
| 2001/0047183 A1 | 11/2001 | Privitera et al. | |
| 2002/0103418 A1 | 8/2002 | Maeda et al. | |
| 2003/0158462 A1 | 8/2003 | Takase | |
| 2003/0187328 A1 | 10/2003 | Seki et al. | |
| 2003/0216617 A1 | 11/2003 | Hirakui et al. | |
| 2004/0073083 A1 | 4/2004 | Ikeda et al. | |
| 2005/0054899 A1 | 3/2005 | Miyake | |
| 2005/0059960 A1 | 3/2005 | Simaan et al. | |
| 2005/0267327 A1 | 12/2005 | Iizuka et al. | |
| 2006/0052664 A1 | 3/2006 | Julian et al. | |
| 2006/0116667 A1 * | 6/2006 | Hamel | A61B 17/320068 606/1 |
| 2006/0161043 A1 * | 7/2006 | Neumann | A61B 1/00133 600/114 |
| 2006/0258955 A1 | 11/2006 | Hoffman et al. | |
| 2007/0167674 A1 | 7/2007 | Toyama | |
| 2007/0232856 A1 | 10/2007 | Ueno et al. | |
| 2007/0238927 A1 | 10/2007 | Ueno et al. | |
| 2008/0103358 A1 | 5/2008 | Suzuki | |
| 2008/0119695 A1 | 5/2008 | Ueno et al. | |
| 2008/0214896 A1 | 9/2008 | Krupa et al. | |
| 2009/0012365 A1 | 1/2009 | Ueno et al. | |
| 2011/0201886 A1 * | 8/2011 | Gumbs | A61B 1/0016 600/118 |

* cited by examiner

REMOTE ENDOSCOPE HANDLE MANIPULATION

CROSS REFERENCE TO RELATED APPLICATIONS

This application is a continuation-in-part of U.S. application Ser. No. 12/866,473, which was filed on Aug. 6, 2010 as the U.S. National Phase Application of PCT/US2009/000749 filed on Feb. 6, 2009, and which issued as U.S. Pat. No. 8,409,080 on Apr. 2, 2013, and claims priority to U.S. Provisional Application No. 61/026,819 filed on Feb. 7, 2008. Each of these applications is incorporated by reference herein, in its entirety and for all purposes.

BACKGROUND OF THE INVENTION

Natural Orifice Transluminal Endoscopic Surgery (NOTES) is a surgical technique in which procedures are performed with an endoscope passed through a natural orifice, such as the mouth, nose, urethra, vagina, or anus, for instance. An endoscope can also be passed though the umbilicus or a single incision, also referred to as Single Port Access (SPA), such as by using a trocar, in some instances. The endoscope can then be passed through an internal incision, such as an incision in the stomach, vagina, bladder, or colon, for instance. By performing NOTES procedures, external incisions or scars can be limited or eliminated altogether.

SUMMARY OF THE INVENTION

The inventors have recognized, among other things, that a factor limiting wider implementation of NOTES is that current endoscopic technology generally involves the presence of two to three doctors (surgeons/endoscopists) to perform a procedure. Most endoscopes were designed to perform relatively simple diagnostic tests and procedures, but were not designed to perform more complex surgeries. To reduce the number of personnel involved in endoscopic procedures, one approach would be to design remotely or robotically controlled endoscopes. However, such technology is not presently commercially available. In addition, the potentially high economic costs of such remotely or robotically controlled endoscopes may be a limiting factor in their widespread adoption. In this document, the inventors describe systems and methods for remote endoscope handle manipulation.

In some embodiments, systems for remote endoscope handle manipulation include a control housing configured to removably attach to an endoscope. A manipulator, associated with the housing, is configured to engage with a control device of the endoscope with the endoscope attached to the housing. An actuator, drivingly coupled with the manipulator, is configured to move the manipulator to operate the control device with the endoscope attached to the housing. The housing may comprise a wireless transmitter and/or wireless receiver or a wireless transceiver for receiving and/or sending wireless signals and wirelessly communicating with a controller to wirelessly operate a control device of the endoscope.

In some embodiments, methods of using a remote endoscope handle manipulation system include attaching a control housing to an endoscope. A manipulator of the control housing is engaged with a control device of the endoscope. The manipulator is controlled to operate the control device of the endoscope.

In some embodiments, systems for remote endoscope handle manipulation include remote controls that control operation of one or more control devices of the endoscope, including gears, buttons, and operational aspects (e.g., irrigation, suction, insufflation, power, camera, light, and combinations thereof) via the control housing without a practitioner using hands to control operation of such control devices. Endoscope handle manipulation preferably is remotely controlled via a practitioner's foot, with the foot being used to operate a foot pedal on a controller. The controller, in turn, is communicatively coupled to the control housing, either through wired electronic communication, mechanical communication, wireless signal communication, or combinations thereof.

Example 1 describes an example of a system for remote endoscope manipulation. In this example, the system can comprise a control housing configured to removably attach to an endoscope. A manipulator can be associated with the housing. The manipulator can be configured to engage with a control device of the endoscope with the endoscope attached to the housing. An actuator can be drivingly coupled with the manipulator. The actuator can be configured to move the manipulator to operate the control device with the endoscope attached to the housing.

In Example 2, the system of Example 1 can optionally be configured such that the manipulator includes a rotational manipulator configured to engage with a rotational control device of the endoscope.

In Example 3, the system of any one or more of Examples 1-2 can optionally be configured such that the rotational manipulator includes a stepper motor.

In Example 4, the system of any one or more of Examples 1-3 can optionally be configured such that the rotational control device includes a gear configured to control movement of a shaft of the endoscope.

In Example 5, the system of any one or more of Examples 1-4 can optionally be configured such that the manipulator includes a translational manipulator configured to engage with a translational control device of the endoscope.

In Example 6, the system of any one or more of Examples 1-5 can optionally be configured such that the translational manipulator includes a solenoid.

In Example 7, the system of any one or more of Examples 1-6 can optionally be configured such that the translational manipulator can be configured to control a translational control device that is configured to control irrigation, suction, or insufflation.

In Example 8, the system of any one or more of Examples 1-7 can optionally comprise a controller communicatively coupled to the housing, the controller configured to send a control signal to the actuator to operate the manipulator or to operate an axial roller.

In Example 9, the system of any one or more of Examples 1-8 can optionally be configured such that the controller includes a foot pedal.

In Example 10, the system of any one or more of Examples 1-9 can optionally be configured such that the control housing is configured to removably attach to an endoscope handle.

In Example 11, the system of any one or more of Examples 1-10 can optionally be configured such that the control housing is configured to partially cover a portion of the endoscope.

In Example 12, the system of any one or more of Examples 1-11 may include an axial roller comprising at least two adjacent sheaves configured to grip and control translational movement of the endoscope shaft, and the sheaves may be operably connected to an axial roller actuator that rotates the sheaves. Rotation of the sheaves, whose grooves are in contact with the endoscope shaft, moves the endoscope shaft forward or backward.

Example 13 describes an example of a method. In this example, the method comprises attaching a control housing to an endoscope, engaging a manipulator of the control housing with a control device of the endoscope, and controlling the manipulator to operate the control device of the endoscope.

In Example 14, the method of Example 13 can optionally be performed such that controlling the manipulator includes using a foot pedal to control the manipulator.

In Example 15, the method of any one or more of Examples 13-14 can optionally be performed such that controlling the manipulator to operate the control device permits controlling movement of a shaft of the endoscope.

In Example 16, the method of any one or more of Examples 13-15 can optionally be performed such that controlling the manipulator to operate the control device permits controlling irrigation, suction, or insufflation using the endoscope.

In Example 17, the method of any one or more of Examples 13-16 can optionally comprise restraining the housing to inhibit movement of a portion of the endoscope.

In Example 18, the method of any one or more of Examples 13-17 can optionally be performed such that attaching the control housing to an endoscope includes attaching the control housing to an endoscope handle.

In Example 19, the method of any one or more of Examples 13-18 can further comprise placing seating the endoscope shaft between at least two sheaves of an axial roller, and controlling the rotation of the sheaves to drive translational movement of the endoscope shaft.

In Example 20, the method of any one or more of Examples 13-19 may be performed such that controlling the rotation of the sheaves includes using a foot pedal to control rotation of the sheaves, for example, by way of an axial roller actuator drivingly coupled to the sheaves.

BRIEF DESCRIPTION OF THE DRAWINGS

The drawings illustrate generally, by way of example, but not by way of limitation, various embodiments discussed herein.

DETAILED DESCRIPTION OF THE INVENTION

It has been observed in accordance with the invention, among other things, that current endoscopic technology involves the presence of two to three doctors (surgeons/endoscopists) to perform a procedure. Robotic endoscopic surgery systems are not yet commercially available and, if or when such systems become available, the costs of such systems may inhibit wide usage of the systems.

Accordingly, the invention features systems and methods for remote or robotic endoscope manipulation and control, which, among other things, can reduce the number of doctors involved in an endoscopic procedure to one or two doctors. Moreover, the systems and methods can make use of existing endoscope devices, thereby reducing additional costs associated with the use of the systems and methods.

In some examples, a system for remote endoscope handle manipulation includes a portion that fits over at least a portion of a handle of an existing endoscope and is configured to manipulate one or more controls on the endoscope handle. In an example, the system includes a controller for a doctor or other operator to use to remotely manipulate the one or more controls on the endoscope handle. In an example, the controller includes a foot pedal to allow the operator to remotely control at least some aspects of the endoscope with a foot, thereby freeing up a hand of the operator, such as to facilitate performing one or more other aspects of the endoscopic procedure.

Figure 2:
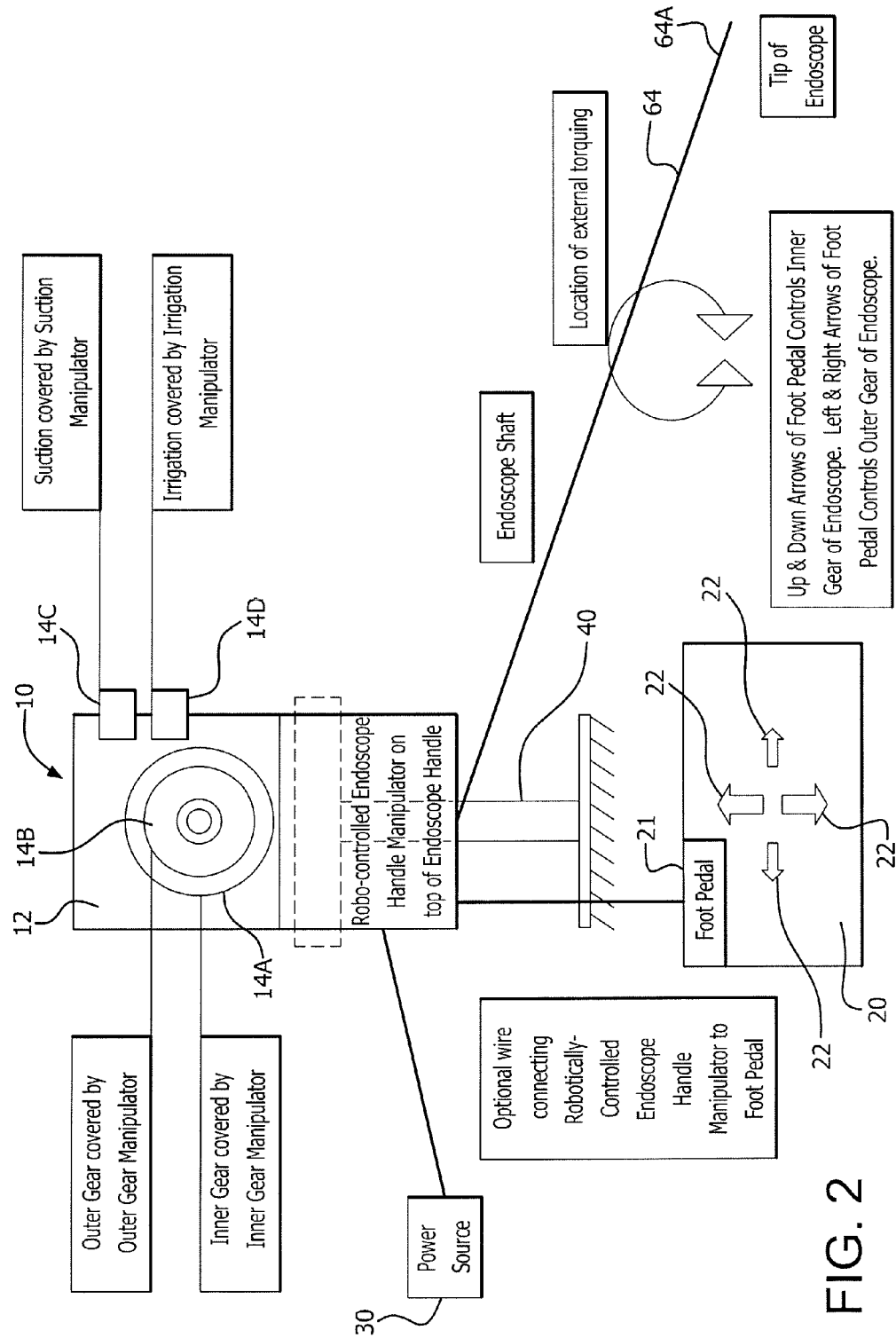
FIG. 2 shows a is a diagrammatic representation of a system for remote endoscope handle manipulation according to some embodiments, the system being attached to an endoscope handle.
Figure 3:
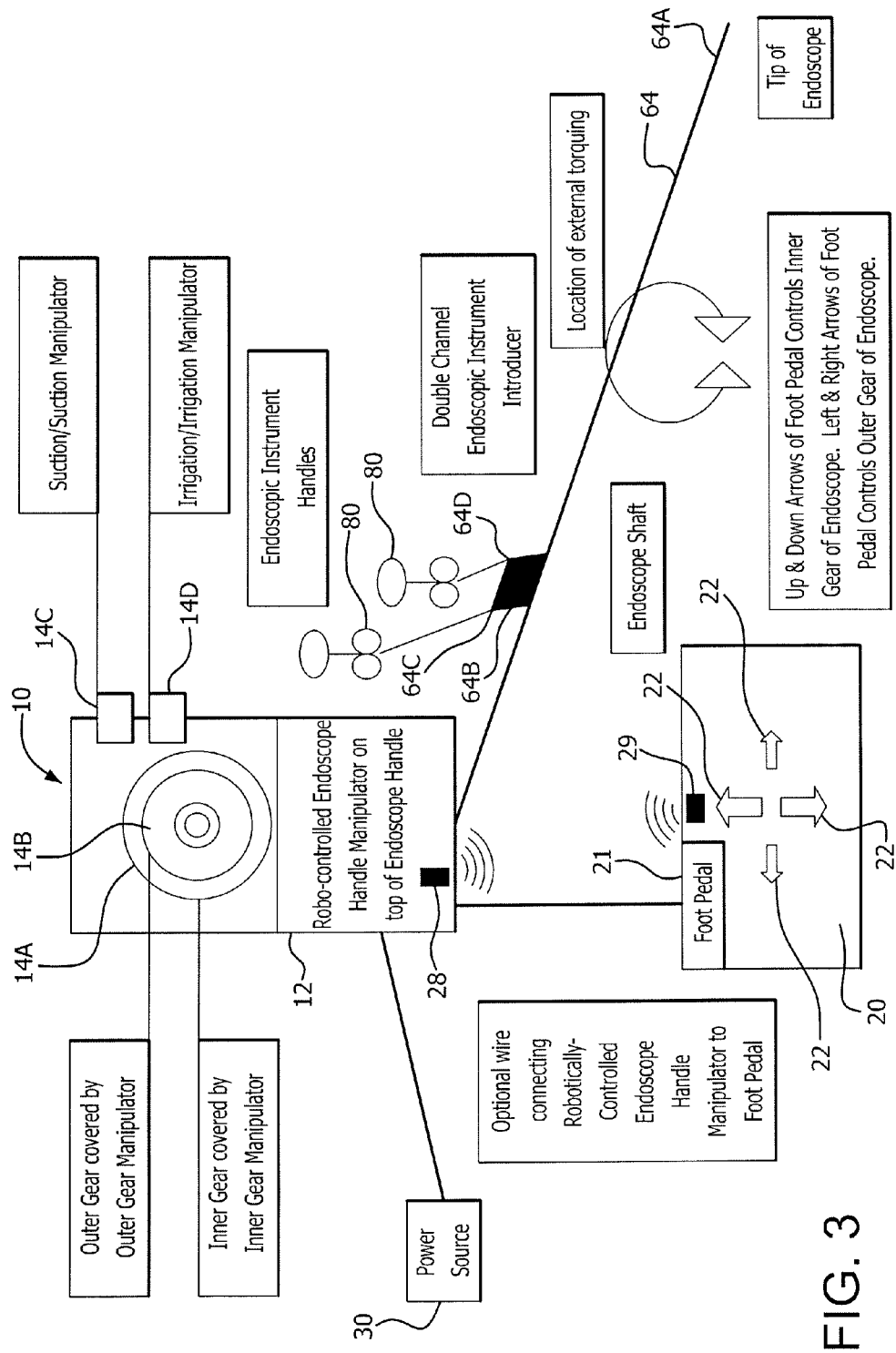
FIG. 3 shows a is a diagrammatic representation of a system for remote endoscope handle manipulation according to some embodiments, the system being attached to an endoscope handle.
Figure 4:
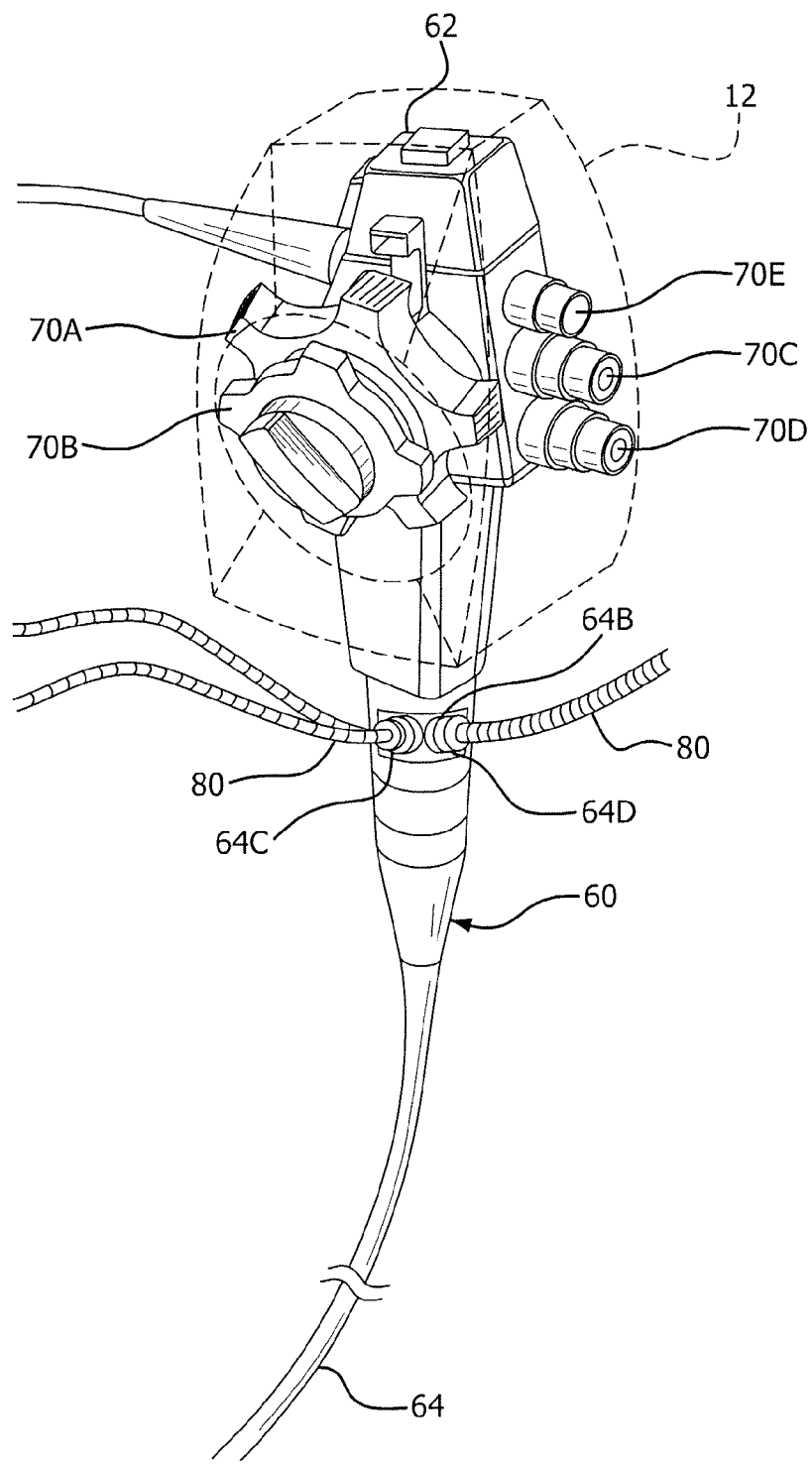
FIG. 4 shows a perspective view of a system for remote endoscope handle manipulation according to some embodiments, the system being attached to an endoscope handle.
Figure 5:
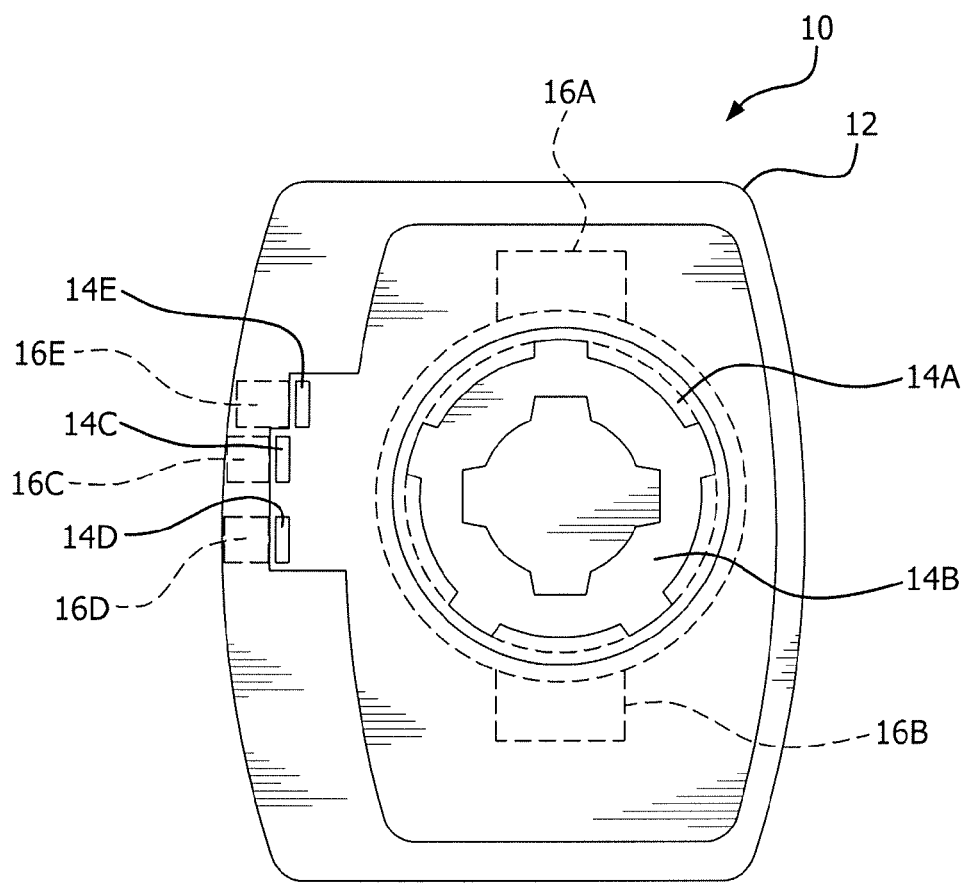
FIG. 5 shows a view of an interior portion of a system for remote endoscope handle manipulation according to some embodiments.

Referring to FIGS. 1-4, in an example, an endoscope 60 includes a shaft 64 and a handle 62 with one or more control devices 70 associated with the handle 62. In an example, the control devices 70 include two gears, such as a first or outer gear 70A and a second or inner gear 70B, that respectively control upward/downward movement and side-to-side movement of a tip 64A of the endoscope shaft 64. The control devices 70 can further include a first button 70C for controlling suction/insufflation and a second button 70D for controlling irrigation. As shown in FIG. 4, the endoscope 60 can further include a third button 70E, which can be used to control another operational aspect of the endoscope 60, such as, for instance, power, camera, light, suction or insufflation (e.g., if suction and insufflation are not controlled with the same control device), or another endoscopic function.

In use, in an example, natural orifice transluminal endoscopic surgeries (NOTES) can be performed by introducing the shaft 64 into a patient's orifice (for instance, the mouth, anus, vagina, or another orifice, or the umbilicus or another incision) and directing the shaft 64 to a desired location within the patient's body, such as by external urging or torquing (FIGS. 2 and 3 depict a possible location along the shaft 64 for such urging or torquing) of the shaft 64 and controlling movements of the tip 64A with the first and second gears 70A, 70B. In an example, as shown in FIGS. 3 and 4, the endoscope 60 includes a port 64C for the introduction of one or more endoscopic devices or tools 80, such as, for instance graspers, endoscopic shears, electrocautery devices, cameras, lights, or other devices or tools. The port 64C can include first and second channels 64C, 64D so that two tools or devices 80 can be inserted into the shaft 64 at the same time. However, the port 64C can include more than or fewer than two channels.

Figure 1:
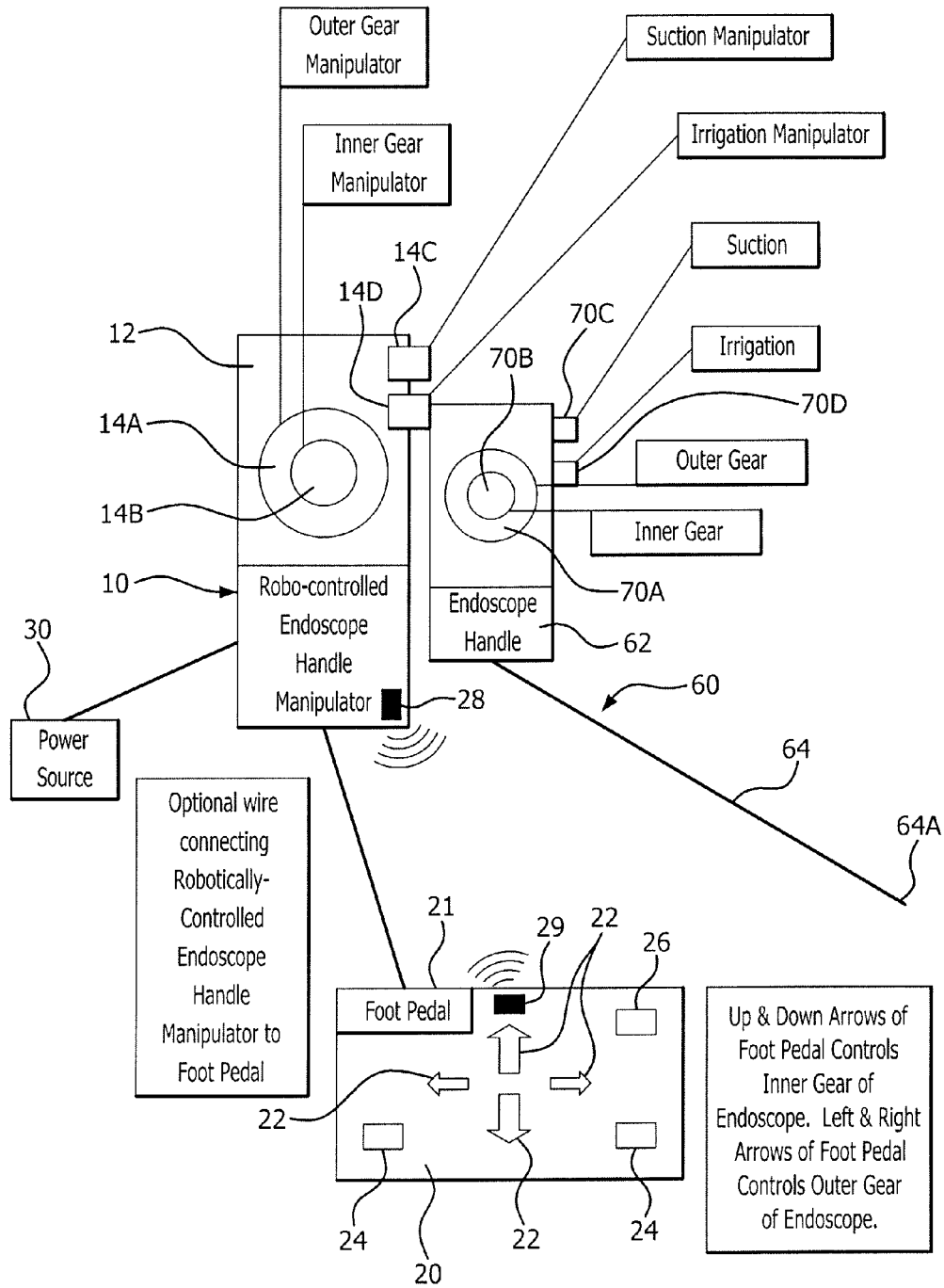
FIG. 1 shows a diagrammatic representation of a system for remote endoscope handle manipulation according to some embodiments, the system being removed from an endoscope handle.

In some examples, the systems 10 attach to an existing flexible endoscope 60 to allow for the first and second gears 70A, 70B of the endoscope 60 to be controlled remotely with a controller 20. In an example, the controller 20 includes a foot pedal interface 21. This can liberate the activity of one operator hand and enable two and possibly even one operator to perform NOTES surgery. In an example, the controller 20 includes one or more controls 22, 24, and 26 such as buttons, pedals, or switches, for instance, which allow the operator to actuate one or more of the actuators of the system 10, for instance, with a foot, to control aspects of the endoscope 60. As shown in FIGS. 1-3, the controls 22 can include four arrow buttons, which can control directional movement of the tip 64A of the endoscope shaft 64. Other controls can be included on the controller 20, such as to control one or more other aspects of the endoscope 60, such as suction, insufflation, irrigation, or operation of one or more endoscopic tools or devices used with the endoscope 60. The controller 20 may also include one or more axial roller controls 26, which may control operation of an axial roller 90, including control of the translational movement of the endoscope handle 64, and thereby including control of the insertion, removal, and depth of the handle 64 within the patient. The controller 20 may include an output 29, for example, a wireless transmitter for transmitting a wireless signal to one or more components of the system capable of receiving a wireless signal. The controller may include a processor (not shown) operably connected to the output as well as the one or more controls 22, 24, and 26, which processor may control generation of the wireless signal in response to operation of such controls 22, 24, and 26 by a user.

In some aspects, the system 10 includes or is coupled to an electrical or other power source 30 to power one or more components of the system 10. The power source 30 can include a plug or other connector for attaching to an external source of power, such as a wall outlet or a generator, or can include one or more batteries.

In some aspects, the systems 10 can include a cradle or holder 40 (FIG. 2) for holding or otherwise restraining movement of the endoscope handle 62. In an example, the handle 62 or other portion of the endoscope 60 or system 10 can be affixed or otherwise attached to or rested upon a portion of the holder 40. Another portion of the holder 40 can then be affixed or otherwise attached to or placed on a table, stand, or other surface. For instance, the holder 40 can include legs or a base for placement on a table, or the holder can include a clamp for fixed attachment to a table. In an example, the holder 40 can be used to hold the endoscope 60 or system 10 during use, for instance, at a particular orientation, so that an operator need not hold the endoscope 60 or system 10. Use of the holder 40 helps further liberate one or more hands of one or more operators, such as to allow an operator to perform one or more other activities.

In some aspects, the systems 10 can be configured to fit one or most standard flexible endoscope handles. For example, endoscopes include inner and outer overlapping gear controls and separate buttons for suction and irrigation control, such as shown in FIGS. 1 and 4.

Referring to FIGS. 1-4, the system 10 includes a housing 12 that is sized and shaped to fit over at least a portion of the endoscope handle 62. FIG. 4 shows an example in which the housing 12 (shown in phantom) is placed over a portion of the handle 62 to control of or otherwise interact with the control devices 70A, 70B, 70C, 70D, 70E of the endoscope 60. The housing 12 can be attached to the endoscope handle 62, for instance, by forming a shell around all or a portion of the handle 62; using one or more straps, clamps, or other attachment devices; using a detent configuration to snap onto the handle 62; or using frictional engagement between the handle 62 and the housing 12. Although shown in FIG. 4 as generally surrounding the handle 62, in some examples, the housing can be a frame or any other structure, including one or more straps, tape, or adhesive, for instance, that can be attached to the handle 62 or other portion of the endoscope 60 to position one or more manipulators, as described below, to allow control of or interaction with the control devices of the endoscope 60.

In some aspects, the housing 12 includes one or more manipulators 14, which are positioned such that they will align with a respective one or more of the control devices 70 of the endoscope 60 when the housing 12 is attached to the handle 62. See, e.g., FIGS. 1-5. For example, a first gear manipulator 14A can be configured to be complementarily shaped and sized to engage with the first gear 70A of the endoscope handle 62, such that rotation of the first gear manipulator 14A causes rotation of the first gear 70A of the endoscope handle 62. In an example, a second gear manipulator 14B can be complementarily shaped and sized to engage with the second gear 70B of the endoscope handle 62, such that rotation of the second gear manipulator 14B causes rotation of the second gear 70B of the endoscope handle 62. In an example, the first and second gear manipulators 14A, 14B are drivingly coupled to first and second actuators 16A, 16B, respectively. For example, an outer edge of each of the first and second gear manipulators 14A, 14B can include gear teeth, which can be engaged by a worm or pinion driven by one of the first and second actuators 16A, 16B. In some aspects, the first or second actuators 16A, 16B can include a rotational actuator, such as a stepper motor, for instance. The first or second actuators 16A, 16B can be independently controlled, such as by actuating different controls 22 on the controller 20, thereby allowing the operator to individually control different aspects of the endoscope 60 using the controller 20.

In some aspects, the systems 10 can include one or more translational manipulators, which align with translational control devices, such as buttons, sliders, or switches, of the endoscope handle 62, with the housing 12 attached to the endoscope handle 62. See, e.g., FIGS. 1-5. In an example, the housing includes first, second, and third button manipulators 14C, 14D, 14E, which are configured to align with the first, second, and third buttons 70C, 70D, 70E, such that translation of the first, second, or third button manipulator 14C, 14D, 14E causes translation of the first, second, or third button 70C, 70D, 70E of the endoscope handle 62. In an example, each of the first, second, and third button manipulators 14C, 14D, 14E provides a surface operably coupled to a driven portion of a translational actuator, such as a solenoid, for instance. In an example, the first button manipulator 14C is coupled to a third actuator 16C, the second button manipulator 14D is coupled to a fourth actuator 16D, and the third button manipulator 14E is coupled to a fifth actuator 16E. The third, fourth, and fifth actuators 16C, 16D, 16E can be independently controlled such as by respective actuating controls 24 (FIG. 1) on the controller 20. This allows the operator to remotely control one or more aspects of the endoscope 60 using the controller 20, without requiring the operator to manipulate controls at the endoscope handle. The number of manipulators and actuators can be increased or decreased, such as to correspond to the number of translational controls on the endoscope. For example, the housing need not include any translational actuators if manual actuation of the translational controls of the endoscope is desired. In this instance, for example, the housing can include an opening therein to allow operator access to one or more of the buttons 70C, 70D, 70E, or can include one or more manipulators that, rather than being coupled to respective actuators, are instead manually operated by the operator from outside of the housing 12.

Once the system 10 is placed over the endoscope handle 62, the system 10 and endoscope handle 62 can be placed in the cradle or holder 40 and the endoscope tip 64A can be robotically-controlled via one or more commands from the controller 20. In another example, the holder or a holding portion is integrated with the control housing or the endoscope (for instance, the endoscope handle), rather than being a separate component. This allows one operator to torque the endoscope shaft 64, as desired, with one hand and to control the one or more endoscopic instruments 80 that are passed through one or more of the channels 64C, 64D with the other hand, thus, permitting a single operator to perform a NOTES procedure or SPA surgery. It is believes that such a system can be cheaper than a fully robotic NOTES endoscope because hospitals can use existing endoscopes with the systems and methods instead of having to invest in new robotic NOTES endoscopes should they become available on the market.

In other examples, the systems can include one or more attachments that can control one or more of the endoscopic instruments 80 passed through one or more of the channels 64C, 64D. In an example, the system includes a device to remotely control the torquing of the endoscopic shaft 64. For instance, one or more actuators can be attached to the endoscopic shaft 64 to urge the shaft in one or more directions, including an axial direction, a rotational direction, and a radial direction, including an axial roller 90. In an example employing the system 10 together with endoscopic instrument control and endoscopic shaft torque control, an existing endoscope can be totally remotely or robotically controlled.

In some aspects, the system 10 includes an axial roller 90. The axial roller 90, which is preferably also remotely controlled, may be used to direct the shaft 64 of the endoscope 60 into and out from the patient into which the shaft 64 has been inserted. For example, the axial roller 90 may move the shaft 64 deeper or more shallow within the patient, as well as into and/or out from the orifice in the patient into which the shaft 64 and tip 64A has been inserted.

Figure 6A:
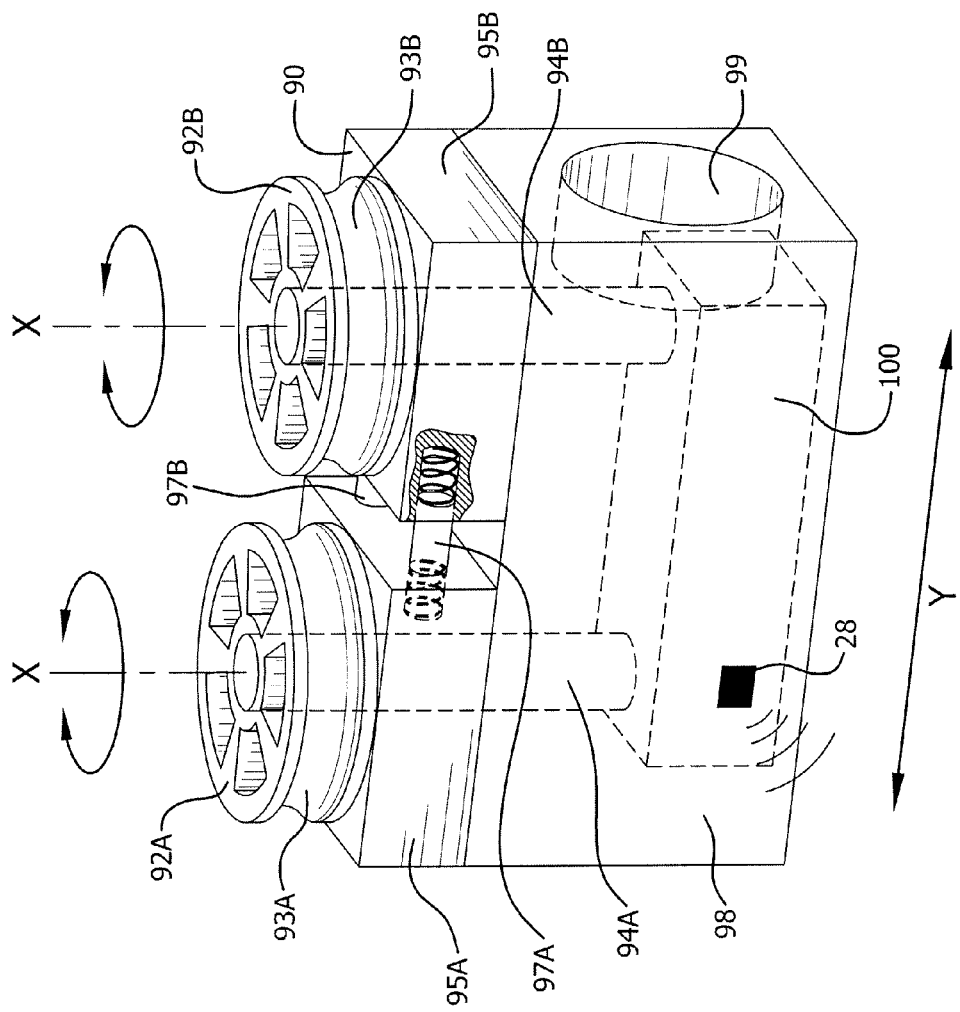
FIG. 6A shows a representation of an axial roller component of the system.

The axial roller 90 comprises at least two sheaves 92A and 92B, each with at least one groove 93A, 93B. See, e.g., FIG. 6A. Each sheave 92A and 92B is mounted on a platen 95B and 95B, and includes an axle 94A and 94B though the center of the sheave 92A and 92B. Each sheave 92A and 92B may freely rotate, independently, in either a clockwise or counterclockwise direction around an axis X. In some aspects, one sheave 92A rotates in a clockwise direction and the other sheave 92B rotates in a counterclockwise direction. In some aspects, both sheaves 92A and 92B rotate in either a clockwise or counterclockwise direction. Rotation may be at any suitable speed, for example, RPMs. The rotation may be facilitated, for example, via turning of the axle 94A and 94B to which each sheave 92A and 92B is attached. In some aspects, at least one of the axles 94A or 94B, and preferably both axles 94A and 94B are operably connected to an axial roller actuator 100. The axial roller actuator 100 may comprise a stepper motor 100, for example, or other suitable motor for rotating one or both axles 94A and 94B. The axial roller actuator 100 may be housed, for example, within an axial roller base 98.

Figure 6B:
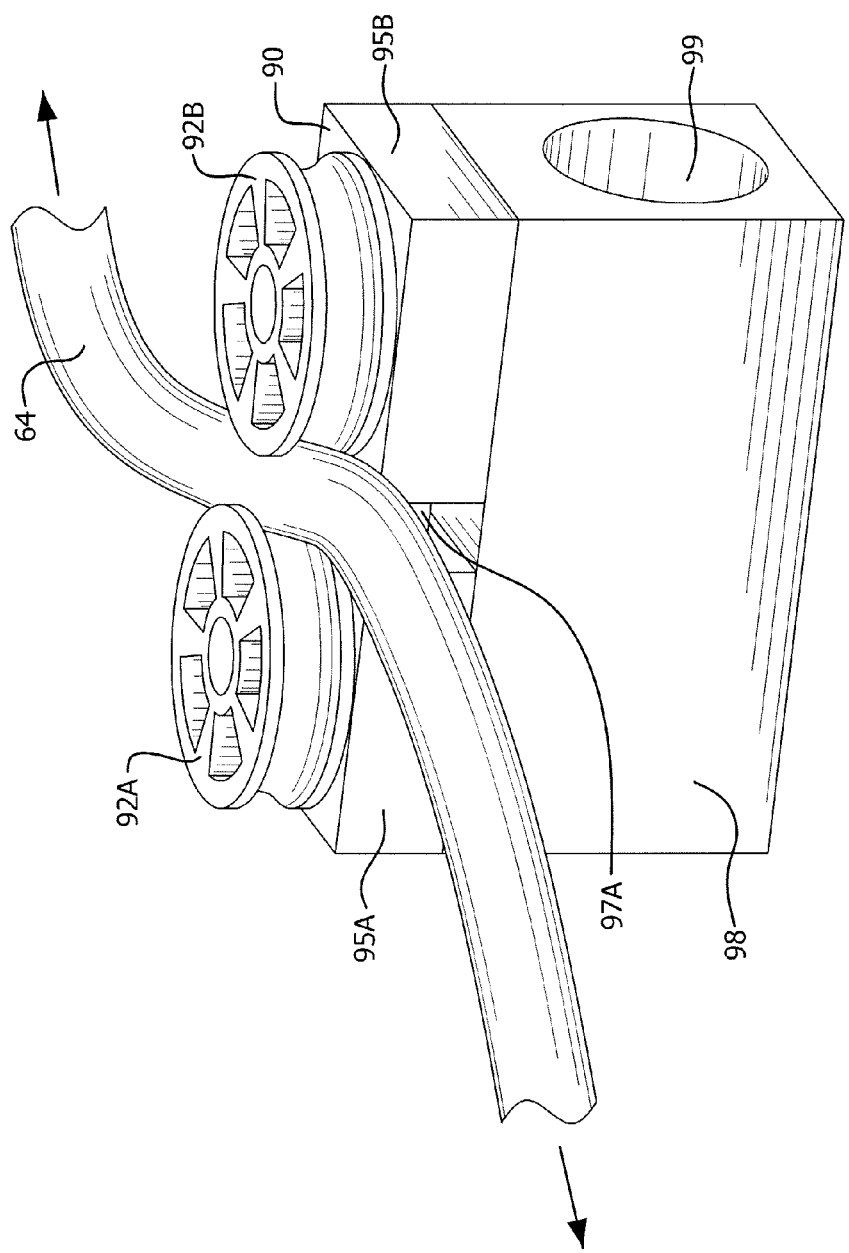
FIG. 6B shows a representation of an axial roller with an endoscope shaft between the sheaves.

In the grooves 93A and 93B, and between each sheave 92A and 92B, the endoscope shaft 64 may be placed. As each sheave 92A and 92B rotates, the shaft 64 may translate in a desired direction which is determined according to the directional rotation of the sheaves 92A and 92B around the axis X. See, e.g., FIG. 6B. To prevent, reduce, or eliminate the possibility of the shaft 64 slipping out from its seating between each sheave 92A and 92B, the grooves 93A and 93B may include a grip, such as a rubber coating, ribbing, or a roughened surface, to enhance a friction fit at the point of contact with the endoscope shaft 64. In some aspects, the axial rollers may include a shaft guard (not shown) that attaches to the base 98 and fits over or around the endoscope shaft 64 to help hold the shaft 64 in place between the sheaves 92A and 92B, for example, to prevent, reduce, or eliminate the possibility of the shaft 64 slipping out from its seating between each sheave 92A and 92B.

Each platen 95A and 95B is preferably mounted on the axial roller base 98. One or both platens 95A and 95B may be movable about the base 98 relative to each other. In some aspects, one platen 95A or 95B is stationary and the other platen 95A or 95B may move. In some aspects, both platens 95A and 95B may move. The platens 95A and 95B may move translationally toward or away from each other about an axis Y. See, e.g., FIG. 6A. By allowing the platens 95A and 95B to be moved apart or closer together, the axial rollers 90 may accommodate different sized endoscope shafts 64, including relatively large and small diametered endoscope shafts 64. For example, by spacing the platens 95A and 95B farther apart, an endoscope shaft 64 with a larger diameter may be seated between the sheaves 92A and 92B, and by spacing the platens 95A and 95B closer together, an endoscope shaft 64 with a smaller diameter may be seated between the sheaves 92A and 92b.

To facilitate the relative movement of the platens 95A and 95B, each platen 95A and 95B may be operably connected together by at least one platen actuator 97. In some aspects, the axial rollers 90 include two platen actuators 97A and 97B. See, e.g., FIG. 6A. In preferred aspects, the platen actuator 97 (or actuators 97A and 97B) may comprise a spring 97 (or springs 97A and 97B). In alternative aspects, the platen actuator 97 (or actuators 97A and 97B) may comprise a rail 97, a piston 97 or a cam 97 or a hydraulic actuator 97, which may be controlled by a motor, including the axial roller actuator 100. The spring 97 is preferred since it passively provides tension that maintains a desired distance between each platen 95A and 95B. The at least one platen actuator 97 may be mounted to each platen 95A and 95B according to any suitable mounting, including a bracket (not shown).

The at least one platen actuator (or actuators 97A and 97B) preferably modulates the distance between each platen 95A and 95B, and thereby allow for the wider or narrower berth into which the endoscope shaft 64 may be placed when connecting the shaft 64 with the sheaves 92A and 92B for purposes of translating the shaft 64, for example, during an endoscopy procedure. In the spring 97 embodiment, the spring tension tends toward pulling each platen 95A and 95B together, and a user may pull the platens 95A and 95B apart to place the shaft 64 within the grooves 93A and 93B of the sheaves 92A and 92B, and when the user releases the platens 95A and 95B, the spring pulls the platens 95A and 95B back toward each other, thereby allowing the grooves 93A and 93B to contact and effectively clamp the shaft 64 in place. In embodiments in which a spring 97 is not used, (e.g., a rail, piston, cam, or hydraulic actuator is used), the movement of platens 95A and 95B either apart or toward each other may be facilitated mechanically by actuation of the piston, cam, or hydraulic actuator, which may necessitate electrical power to establish the tension that would otherwise be established by the relative stiffness, e.g., spring constant, of the spring 97 when a spring 97 is used.

The axial rollers 90 may be mounted near to the area in which the endoscope shaft 64 will be inserted into the patient. In some aspects, the axial roller base 98 is mounted to this area. For example, the axial roller base 98 may be mounted to a bed or table on which the patient will lie during the endoscopic procedure, or may be mounted to a pole or other structure that would be positioned proximal to the bed or table.

Figure 7A:
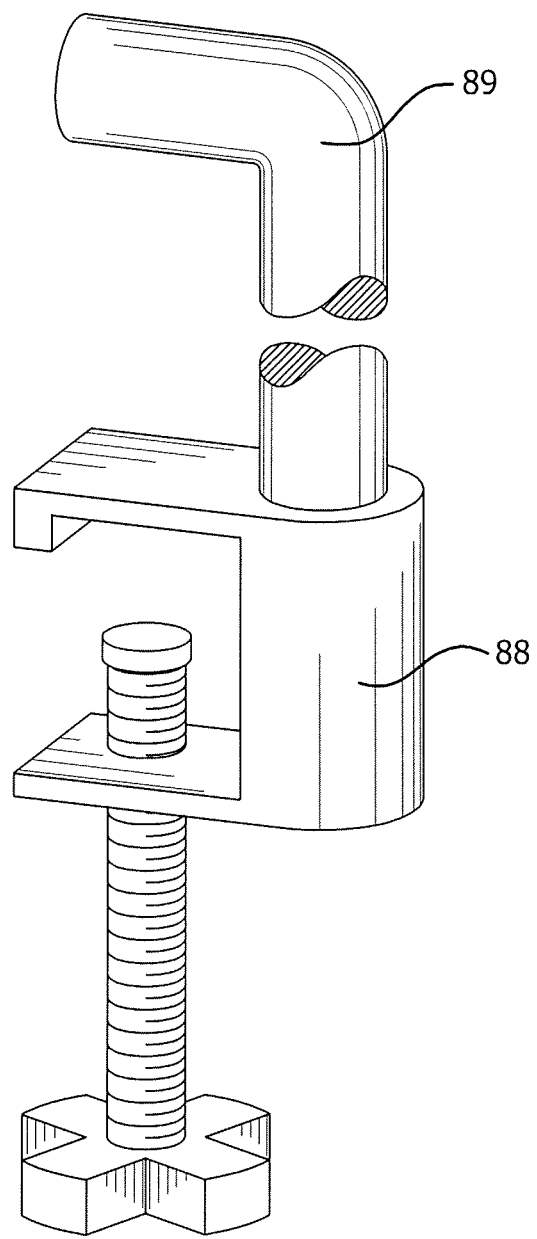
FIG. 7A shows an example of a clamp for affixing an axial roller in place during an endoscopy procedure.
Figure 7B:
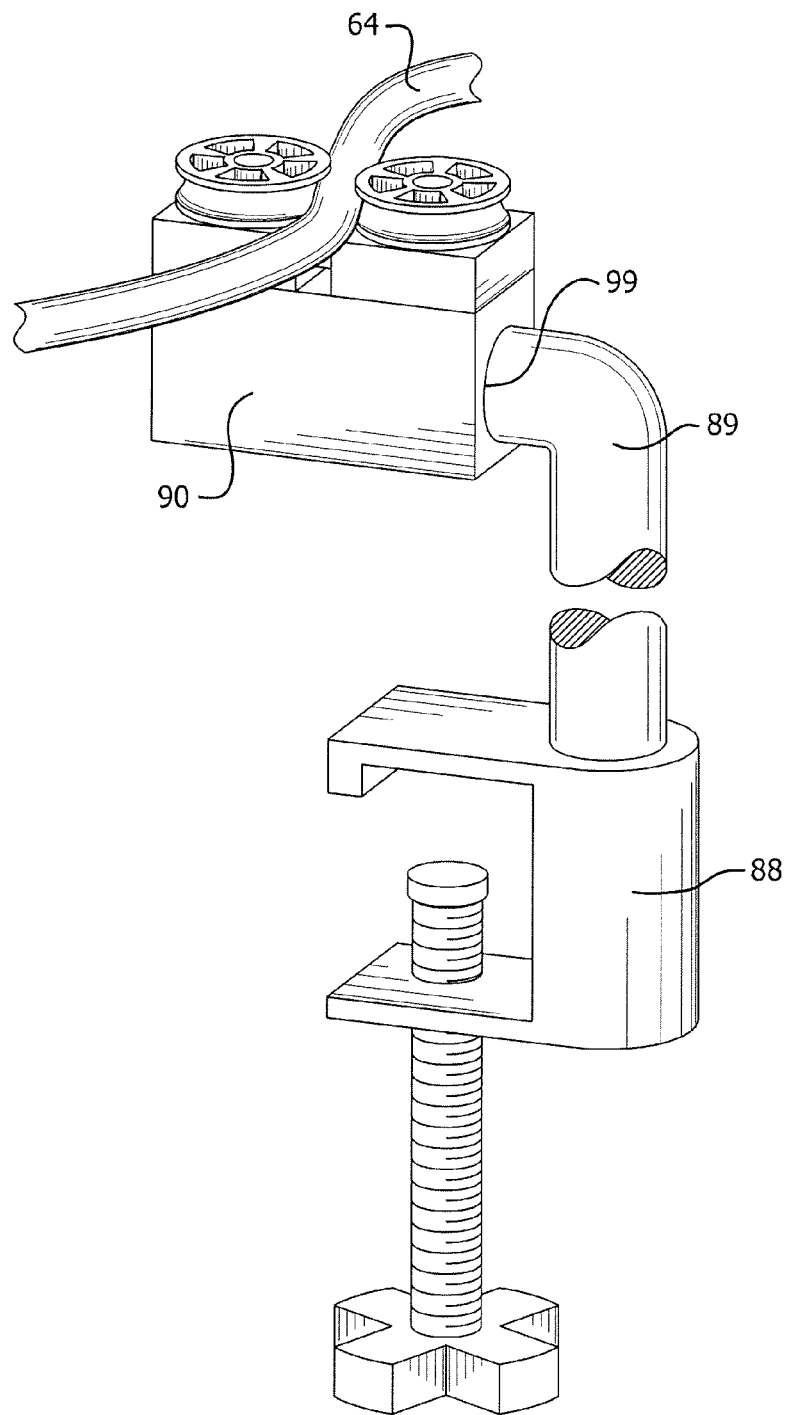
FIG. 7B shows an example of the clamp connected to the axial roller.

To enhance stability of the mounting of the axial roller base 98, a clamp 88 may be used, which connects to both the base 98 and another support such as a bed, table, pole, or other suitable support. See, e.g., FIG. 7. The clamp 88 may be joined to a connector 99 on the axial roller base 98. See, e.g., FIG. 6A, FIG. 7A, and FIG. 7B. The clamp 88 may be joined to the connector 99 by way of an arm 89, which arm 89 may be rigid, flexible, or modular. FIG. 7B. The modules may allow the arm 89 to accommodate different shapes, sizes, and locations of the substrata to which the base 98 may be connected.

In some examples, methods of using the remote endoscope handle manipulation system 10 include attaching the control housing 12 to the handle 12 of the endoscope 60, such that at least one manipulator 14A, 14B, 14C, 14D, or 14E of the control housing 12 engages a corresponding control device 70A, 70B, 70C, 70D, or 70E of the endoscope handle 62. As well, the methods may include connecting the endoscope shaft 64 within the axial rollers 90. The operator can remotely control at least one manipulator 14A, 14B, 14C, 14D, or 14E to remotely operate at least one control device 70A, 70B, 70C, 70D, or 70E of the endoscope handle 62. The operator can also remotely control the axial roller actuator 100 to remotely control the insertion and/or depth of the endoscope shaft 64 in the patient.

In one example, the operator uses a controller 20 to operate at least one control device 70A, 70B, 70C, 70D, or 70E of the endoscope handle 62, and may also use the controller 20 to operate the axial roller 90, for example, by way of controlling the actuation of the sheaves 92A and 92B on the axial roller 90. In some aspects, the controller 20 comprises a foot pedal interface 21 to allow the operator to operate one or more aspects of the endoscope 60 by foot, thereby freeing up use of an arm or hand of the operator. The foot pedal interface 21 may comprise the one or more controls 22 and 24 and the axial roller control 26. Thus, by using the foot pedal interface 21 on the controller 20, which is communicatively coupled to the control housing 12, the user may rotate the gears 70A and 70B by causing the controller 20 to communicate with one or more rotational actuators 16A and 16B to rotate one or more rotational manipulators 14A and 14B such that rotation of the one or more rotational manipulators 14A and 14B rotates the gears 70A and 70B, and the user may operate an operational aspect of the endoscope 60 by causing the controller 20 to communicate with one or more translational actuators 16C, 16D, and 16E to translate one or more button manipulators 14C, 14D, and 14E such that translation of the one or more button manipulators 14C, 14D, and 14E translates the one or more buttons 70C, 70D, and 70E. As well, by using the foot pedal interface 21 on the controller 20, which is communicatively coupled to the axial roller 90, the user may rotate the sheaves 92A and 92B by causing the controller 20 to communicate with the axial roller actuator 100 to rotate the axles 94A and 94B such that rotation of the axles 94A and 94B rotates the sheaves 92A and 92B such that the endoscope shaft 64 may be translated into, out from, or within the patient.

In some aspects, the operator can restrain at least a portion of the system 10, such as to inhibit movement of the endoscope handle 62. In an example, the system 10 may be restrained using the holder 40, such as described above. Aspects of the system 10 such as the axial roller 90 may be restrained using the clamp 88. In this way, the operator can free-up use of a hand to allow the operator to control one or more additional endoscope operations, thereby potentially decreasing the number of operators required to perform a NOTES or other endoscopic procedure.

Although the controller 20 is described above as electrically communicating with actuators 16A, 16B, 16C, 16D, 16E, 97, and 100 to manipulate the various components of the system 10, in some examples, the controller 20 can mechanically communicate with the manipulators 14A, 14B, 14C, 14D, and 14E, such as by using rotating shafts or translating wires, rods, or shafts to mechanically deliver drive power from the controller 20 to the manipulators 14A, 14B, 14C, 14D, and 14E. The shafts, rods, or wires can be mechanically rotated or translated using actuators 16A, 16B, 16C, 16D, 16E, 97, and 100, such as stepper motors or solenoids, for instance, associated with the controller 20.

In some aspects, the controller 20 wirelessly communicates with the actuators 16A, 16B, 16C, 16D, 16E, 97, and 100, including one or more of the translational actuators 16C, 16D, and 16E, rotational actuators 16A and 16B, axial roller actuator 100, and platen actuators 97. Thus, for example, each of the translational actuators 16C, 16D, and 16E, rotational actuators 16A and 16B, axial roller actuator 100, and platen actuators 97 may comprise an input 28, for example, a wireless receiver or transceiver, for receiving a control signal (e.g., radio signal or other suitable wireless signal), from the controller 20 and may comprise a processor that causes and controls activation, or cessation of activation, of the particular actuator 16A, 16B, 16C, 16D, 16E, 97, and 100 in response to the control signal. In this respect, the controller 20 may comprise an output 29, for example, a transmitter or transceiver, for sending a control signal independently to each respective input 28 on each respective actuator 16A, 16B, 16C, 16D, 16E, 97, and 100. The controller 20 may comprise a processor that controls wireless signaling.

Thus, for example, the operator may use the foot pedal interface 21 to control operation of the system 10 and its respective components as described and exemplified herein, including by pressing (e.g., with a foot) the controls 22, 24 and the axial roller control 26. Through the processor and output 29 of the controller 20, the controller 20 may send a wireless signal to any input 28 on an actuator 16A, 16B, 16C, 16D, 16E, 97, and 100 to control activation of the actuator 16A, 16B, 16C, 16D, 16E, 97, and 100.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, examples in which only those elements shown and described are provided have been contemplated.

In this document, the terms "a" or "an" include plural referents. The term "or" is used to refer to a nonexclusive or, such that "A or B" includes "A but not B," "B but not A," and "A and B," unless otherwise indicated.

The above description is intended to be illustrative, and not restrictive. For example, the above-described examples (or one or more aspects thereof) may be used in combination with each other. Other embodiments can be used, such as by one of ordinary skill in the art upon reviewing the above description.

We claim:

1. A system for remote endoscope manipulation, the system comprising:
an endoscope including a shaft having a tip and a handle having gears for moving the tip in an upward, downward, and side-to-side direction and having one or more buttons for operating an operational aspect of the endoscope including irrigation, suction, insufflation, power, a camera, a light, or a combination thereof;
a control housing removably attached to the endoscope handle;
one or more rotational manipulators on the housing configured to engage the gears, and one or more button manipulators on the housing configured to engage the one or more buttons when the housing is attached to the endoscope handle; one or more rotational actuators drivingly coupled to the one or more rotational manipulators such that actuation of said one or more rotational actuators rotates the one or more rotational manipulators and rotation of the one or more rotational manipulators rotates the gears, and one or more translational actuators drivingly coupled to the one or more button manipulators such that actuation of said one or more translational actuators translates the one or more button manipulators and translation of the one or more button manipulators translates the one or more buttons, thereby operating an operational aspect of the endoscope;
an axial roller comprising two sheaves for translating the endoscope shaft and an axial roller actuator drivingly coupled to the sheaves such that actuation of said axial roller actuator rotates the two sheaves, thereby translating the endoscope shaft wherein one of the two sheaves is mounted on a first platen and the other of the two sheaves is mounted on a second platen, and the first platen and the second platen are operably connected to at least one platen actuator such that actuation of said platen actuator moves the first platen apart from the second platen along a rectilinear path;
and a controller communicatively coupled to the housing and configured to communicate with and cause actuation of the one or more rotational actuators and the one or more translational actuators and thereby rotate the gears and operate an operational aspect of the endoscope, communicatively coupled to the at least one platen actuator and cause actuation of the at least one platen actuator, and communicatively coupled to the axial roller and configured to communicate with and cause actuation of the axial roller actuator, the controller including a foot pedal that allows an operator of the system to remotely rotate the gears, operate an operational aspect of the endoscope, and translate the endoscope shaft by foot.

2. The system of claim 1, wherein the one or more rotational actuators drivingly coupled to the one or more rotational manipulators include a stepper motor.

3. The system of claim 1, wherein the one or more translational actuators drivingly coupled to the one or more button manipulators include a solenoid.

4. The system of claim 1, wherein the axial roller actuator drivingly coupled to the sheaves includes a stepper motor.

5. The system of claim 1, wherein the control housing is configured to partially cover a portion of the endoscope.

6. The system of claim 1, further comprising a holder for holding or restraining movement of the endoscope handle.

7. The system of claim 6, wherein the holder is integral with the control housing.

8. The system of claim 1, further comprising a clamp for holding or restraining movement of the axial roller.

9. The system of claim 1, wherein the endoscope further includes a port for one or more of a grasper, endoscopic shears, electrocautery device, camera, or light.

10. The system of claim 9, wherein the port comprises two channels.

11. The system of claim 1, wherein the system further comprises a power source.

12. The system of claim 1, wherein the one or more rotational manipulators include gear teeth.

13. The system of claim 1, wherein the controller electronically communicates with and causes actuation of the one or more rotational actuators, the one or more translational actuators, the at least one platen actuator, and the axial roller actuator.

14. The system of claim 1, wherein the controller mechanically communicates with and causes actuation of the one or more rotational actuators, the one or more translational actuators, the at least one platen actuator, and the axial roller actuator.

15. The system of claim 1, wherein the controller wirelessly communicates with and causes actuation of the one or more rotational actuators, the one or more translational actuators, and the axial roller actuator.

16. The system of claim 1, wherein the foot pedal includes arrow buttons for controlling the direction of movement of the endoscope tip and includes buttons for controlling the direction of translation of the endoscope shaft.

17. The system of claim 1, wherein the system comprises two platen actuators, and each platen actuator comprises a spring.

18. The system of claim 1, wherein the at least one platen actuator comprises a piston or hydraulic actuator.

19. A system for remote endoscope manipulation, the system comprising:
an endoscope including a shaft having a tip and a handle having gears for moving the tip in an upward, downward, and side-to-side direction and having one or more buttons for operating an operational aspect of the endoscope including irrigation, suction, insufflation, power, a camera, a light, or a combination thereof;
a control housing removably attached to the endoscope handle;
one or more rotational manipulators on the housing configured to engage the gears, and one or more button manipulators on the housing configured to engage the one or more buttons when the housing is attached to the endoscope handle; one or more rotational actuators drivingly coupled to the one or more rotational manipulators such that actuation of said one or more rotational actuators rotates the one or more rotational manipulators and rotation of the one or more rotational manipulators rotates the gears, and one or more translational actuators drivingly coupled to the one or more button manipulators such that actuation of said one or more translational actuators translates the one or more button manipulators and translation of the one or more button manipulators translates the one or more buttons, thereby operating an operational aspect of the endoscope;

an axial roller comprising two sheaves for translating the endoscope shaft and an axial roller actuator drivingly coupled to the sheaves such that actuation of said axial roller actuator rotates the two sheaves, thereby translating the endoscope shaft wherein one of the two sheaves is mounted on a first platen and the other of the two sheaves is mounted on a second platen, and the first platen and the second platen are operably connected to at least one platen actuator such that actuation of said platen actuator moves the first platen apart from the second platen along a rectilinear path;

and a controller wirelessly communicatively coupled to the housing and configured to wirelessly communicate with and cause actuation of the one or more rotational actuators and the one or more translational actuators and thereby rotate the gears and operate an operational aspect of the endoscope, and wirelessly communicatively coupled to the at least one platen actuator and cause actuation of the at least one platen actuator, the controller including a foot pedal that allows an operator of the system to remotely rotate the gears and operate an operational aspect of the endoscope by foot.

20. The system of claim 19, wherein the system comprises two platen actuators, and each platen actuator comprises a spring.

21. The system of claim 19, wherein the at least one platen actuator comprises a piston or hydraulic actuator.

* * * * *